United States Patent [19]

Tsurumi et al.

[11] 4,092,220
[45] May 30, 1978

[54] PROCESS FOR MANUFACTURE OF L(+)-TARTARIC ACID OR SALTS THEREOF

[75] Inventors: Yoshihiro Tsurumi, Tokyo; Tomio Fujioka, Matsudo, both of Japan

[73] Assignee: Mitsubishi Gas Chemical Co., Inc., Tokyo, Japan

[21] Appl. No.: 677,834

[22] Filed: Apr. 16, 1976

[30] Foreign Application Priority Data

Apr. 16, 1975   Japan .................................. 50-46030

[51] Int. Cl.² .............................................. C12D 1/02
[52] U.S. Cl. .................................................. 195/30
[58] Field of Search .......................................... 195/30

[56] References Cited

U.S. PATENT DOCUMENTS

| | | | |
|---|---|---|---|
| 3,767,790 | 10/1973 | Guttag | 195/100 |
| 3,957,579 | 5/1976 | Sato et al. | 195/30 |
| 4,010,072 | 3/1977 | Miura et al. | 195/30 |

*Primary Examiner*—Alvin E. Tanenholtz
*Attorney, Agent, or Firm*—Birch, Stewart, Kolasch and Birch

[57] ABSTRACT

Conversion of cis-epoxysuccinic acid or salts thereof into L(+)-tartaric acid or salts thereof is obtained by the agency of hydrolase.

12 Claims, 2 Drawing Figures

PROCESS FOR MANUFACTURE OF L(+)-TARTARIC ACID OR SALTS THEREOF

This invention relates to a process for the manufacture of L(+)-tartaric acid or salts thereof, which comprises causing a novel hydrolase to react upon cis-epoxysuccinic acid or salts thereof for thereby producing specifically L(+)-tartaric acid or salts thereof and collecting the products.

L(+)-tartaric acid is extensively used in large quantities as medicine and food additives and also as industrial raw materials.

Heretofore, L(+)-tartaric acid has solely been manufactured by a process utilizing as the raw material the raw tartar which is by-produced in the production of wine. The amount of supply by this process has its limit. It is observed that the supply of this compound has become increasingly tighter on the worldwide scale as a result of the recent increase of demand. In the circumstances, the price thereof is continuing to increase. The tartaric acid which is obtained by the technique of organic synthetic chemistry is generally an optically inactive DL-tartaric acid. This DL-tartaric acid has a lower solubility than L(+)-tartaric acid and, therefore, is disadvantageous for commercial uses. As a food additive such as for refreshing beverages, for example, it is still susceptible of doubts in terms of safety, palatability, etc. So far, no commercially advantageous process for the production of L(+)-tartaric acid has been suggested to the art, with the exception of the process using as the raw material the raw tartar which is limited in amount of supply.

It is an object of the present invention to provide a process which permits the production on a commercial scale of L(+)-tartaric acid or L(+)-tartrates usable as the raw material for L(+)-tartaric acid.

According to the present invention, there is provided a process for the manufacture of L(+)-tartaric acid or salts thereof, which process comprises causing an enzyme capable of hydrolyzing the epoxy group of cis-epoxysuccinic acid or salts thereof to react upon cis-epoxysuccinic acid or salts thereof to produce L(+)-tartaric acid or salts thereof and collecting the products. According to the present invention, L(+)-tartaric acid and salts thereof which are important from the commercial point of view can easily be produced in large quantities in high yields and with high selectivities. Thus, this invention has an extremely high commercial value.

The enzyme in the present invention which is capable of hydrolyzing the epoxy group of cis-epoxysuccinic acid or salts thereof (hereinafter referred to as "cis-epoxysuccinic acid-hydrolase") is a novel enzyme discovered by the present inventors. It possesses an activity to bring about asymmetric hydrolysis and ring cleavage on the epoxy group of cis-epoxysuccinic acid or salts thereof.

In the accompanying drawing.

The cis-epoxysuccinic acid-hydrolase which is used in the present invention is possessed of the properties indicated in Table 1 and the origin thereof is unrestricted. The form in which the enzyme is used is not particularly limited, either. Generally, however, it can be used in the form of culture broth, live microbic cells, dried microbic cells, cell free extract, refined enzyme liquid, immobilized enzyme or gel entrapped microorganism, etc.

Table 1

Figure 1:
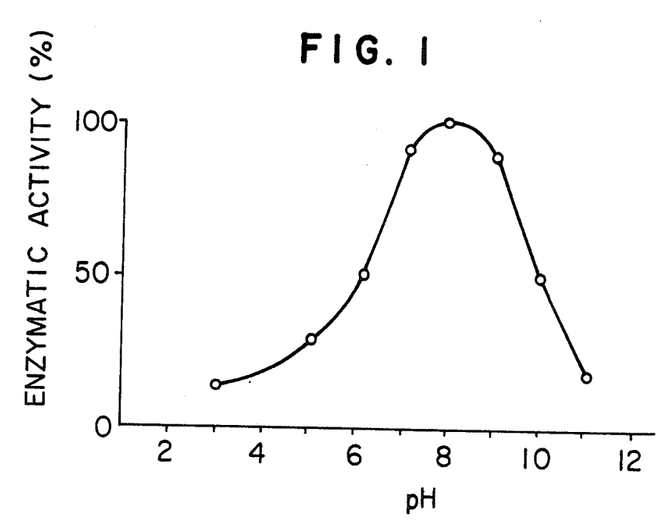
FIG. 1 is a graph showing the enzymatic activity of the cis-epoxysuccinic acid-hydrolase used in the present invention as the function of pH value and FIG. 2 is a graph showing the enzymatic activity of the cis-epoxysuccinic acid-hydrolase use in the present invention as the function of temperature.
Figure 2:
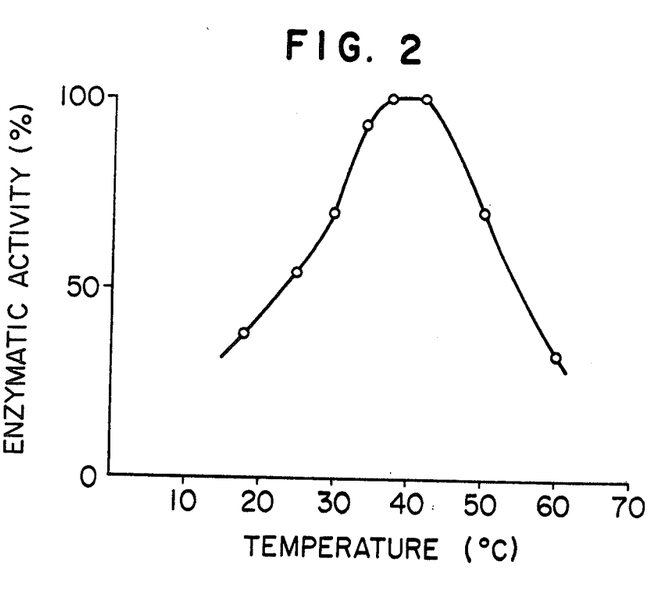

| Enzymatic properties | |
|---|---|
| (1) Activity | Converts cis-epoxysuccinic acid or salts thereof into L(+)-tartaric acid or salts thereof by effecting asymmetric hydrolysis and ring cleavage of the epoxy group of cis-epoxysuccinic acid or salts thereof. |
| (2) Substrate specificity | Effects no activity on trans-epoxysuccinic acid, maleic acid, fumaric acid and salts thereof. |
| (3) pH | Optimum pH 8, stable at pH 3–11 (cf. FIG. 1) |
| (4) Measurement of enzymatic activity | Obtained by causing the enzyme to react, at pH 8.0, upon cis-epoxysuccinic acid or a salt thereof, determining the amount of produced L(+)-tartaric acid or salts thereof such as by titration with periodic acid and expressing the result in terms of amont of produced L(+)-tartaric acid or salt thereof in m.mol/min./mg (ml) of enzyme used. |
| (5) Range of suitable working temperatures | 25 – 55° C (60° C tolerable for the maximum period of 20 minutes). |
| (6) Inactivating temperature | Inactivated after 24 hours of standing at 65° C. |
| (7) Inhibitor | PCMB (p-chloromercuribenzoic acid) |
| (8) Method for purification | Purification was carried out by breaking cultured cells with a homogenizer, extracting the homogenate by centrifugation, fractionating the extract with ammonium sulfate by an ordinary method, dialyzing the fraction to separate crude enzyme solution and refining this crude enzyme solution by means of column chromatography using either diethylaminoethyl cellulose or dextran gel*. |
| (9) Michaelis constant | $1.47 \times 10^{-2}$ M/l |

*Concrete examples of dextran gel are diethylaminoethyl-Sephadex and Sephadex G-100 (Pharmacia Fine Chemicals).

The bacteriological properties respectively of *Acetobacter curtus* No. 4 (FERM-P No. 2879), *Acetobacter curtus* No. 10 (FERM-P No. 2880) and *Acetobacter curtus* No. 21 (FERM-P No. 2881), all new microbic species belonging to the genus Acetobacter which the present inventors have used as typical sources of cis-epoxysuccinic acid-hydrolase are shown in Table 2. And those of *Corynebacterium* S-13 (FERM-P No. 2891), a new microbic species belonging to genus Corynebacterium which has similarly been used are shown in Table 3.

Table 2

| | Bacteriological properties | | |
|---|---|---|---|
| Deposit No. | FERM-P No. 2879 | FERM-P No. 2880 | FERM-P No. 2881 |
| [I] Morphological properties | | | |
| (1) Cell shape | Short rod | Short rod | Short rod |
| (2) Cell size | (0.3 – 0.4) micron x (0.6 – 1.0) micron | Same as left | (0.2 – 0.4) micron x (0.6 – 0.8) micron |
| (3) Motility | None | None | None |
| (4) Flagellum | None | None | None |
| (5) Spore | None | None | None |
| (6) Metachromatic granules | None | None | None |
| (7) Gram's stain | Negative | Negative | Negative |
| (8) Acid fast stain | Negative | Negative | Negative |
| [II] Growth state on various cultural media | | | |
| (1) Bouillon agar | Circular | Same as left | Same as left |

Table 2-continued

| | Bacteriological properties | | |
|---|---|---|---|
| Deposit No. | FERM-P No. 2879 | FERM-P No. 2880 | FERM-P No. 2881 |
| plate culture | colonies | | |
| | Entire edge | Same as left | Same as left |
| | Smooth surface | Same as left | Same as left |
| | Hemispherically raised | Same as left | Same as left |
| | Lustrous | Same as left | Same as left |
| | Opaque | Same as left | Same as left |
| | Milky white | Same as left | Same as left |
| (2) Bouillon agar slant culture | Linear growth | Same as left | Same as left |
| | Milky white | Same as left | Same as left |
| | Lustrous | Same as left | Same as left |
| | No change in medium | Same as left | Same as left |
| (3) Bouillon agar stab culture | Linear growth close to surface | Same as left | Same as left |
| (4) Bouillon gelatin stab culture | Linear growth close to surface without liquefaction | Same as left | Same as left |
| (5) Bouillon liquid stationary culture | Uniformly, slightly turbid | Same as left | Same as left |
| (6) Litmus milk test | No change | Same as left | Same as left |
| [III] Physiological properties | | | |
| (1) Reduction of nitrate | + | − | − |
| (2) Denitrification | − | − | − |
| (3) MR test | − | − | − |
| (4) VP test | − | − | − |
| (5) Formation of indole | − | − | − |
| (6) Formation of hydrogen sulfide | − | − | − |
| (7) Hydrolysis of starch | − | − | − |
| (8) Utilization of citric acid (by combined use of Koser medium and Christensen medium) | + | ++ | + |
| (9) Utilization of inorganic nitrogen sources (nitrates and ammonium salts) | + | + | + |
| (10) Formation of pigment | − | − | − |
| (11) Urease | + | ++ | + |
| (12) Oxidase | + | + | + |
| (13) Catalase | − | − | − |
| (14) Phenylalanine deaminase. | − | − | − |
| (15) Hydrolysis of sorbitan monooleate polyoxyethylene (available under trademark at Tween 80") | − | − | − |
| (16) A) pH for growth | 3.7 − 7.5 | Same as left | Same as left |
| B) Optimum pH for growth | 5.5 − 6.5 | Same as left | 5.0 − 6.5 |
| (17) A) Temperature for growth | 15 − 36° C | Same as left | Same as left |
| B) Optimum temperature for growth | 30 ± 3° C | Same as left | Same as left |
| (18) Behavior to oxygen | Aerobic | Same as left | Same as left |
| (19) O-F test (by Hugh-Leifson method) | | | |
| 1) L-arabinose | + | + | + |
| 2) D-xylose | + | + | + |
| 3) D-glucose | + | + | + |
| 4) D-mannose | + | + | + |
| 5) D-fructose | − | − | − |
| 6) D-galactose | ++ | +++ | + |
| 7) Maltose | − | − | − |
| 8) Sucrose | − | − | − |
| 9) Lactose | ± | + | ± |
| 10) D-trehalose | − | − | − |
| 11) D-sorbitol | − | − | − |
| 12) D-mannitol | − | − | − |
| 13) Inositol | − | − | − |
| 14) Glycerine | − | − | − |
| 15) Starch | − | − | − |
| | No gas production from any of the foregoing sugars observed. | | |
| (20) Assimilability of alcohols | | | |
| 1) Methanol | − | − | − |
| 2) Ethanol | + | + | + |
| 3) Propanol | − | − | − |
| 4) Butanol | − | − | − |
| 5) Iso-butanol | − | − | − |
| (21) Assimilability of organic acids | | | |
| 1) Acetic acid | − | − | − |
| 2) Lactic acid | + | + | + |
| 3) Pyruvic acid | + | + | + |
| 4) Butyric acid | − | − | − |
| 5) Gluconic acid | ++ | ++ | ++ |
| 6) L(+)-tartaric acid | + | + | + |
| 7) Cis-epoxysuccinic acid | + | + | + |
| (22) Other properties | | | |
| 1) Oxidation of ethanol to acetic acid at pH 4.5 | + (weak) | + (weak) | + (weak) |
| 2) Oxidation of lactic acid to $CO_2$ | + | + | + |
| 3) Production of acetic acid from glucose | + | + | + |
| 4) Production of 2-ketogluconic acid from gluconic acid | − | − | − |
| 5) Production of 5-ketogluconic acid from glucose | − | − | ' |
| [IV] Source of isolation | Soil | Same as left | Same as left |

Table 3

| | Bacteriological Properties |
|---|---|
| Deposit No. | FERM-P No. 2891 |
| [I] Morphological properties | |
| (1) Cell shape | Pleomorphic long rod possibly assuming V-shaped, Y-shaped or palisad arrangement. |
| (2) Cell size | (0.4 − 0.7) micron × (1.0 − 8.0) micron |
| (3) Motility | None |
| (4) Flagellum | None |
| (5) Production of spore | None |
| (6) Metachromatic granules | Several granules |
| (7) Gram's stain | Positive |
| (8) Acid resistance | Negative |
| [II] Growth state on various culture media | |
| (1) Bouillon agar plate culture | Colonies circular Entire edge Coarse surface Raised in creases Lustrous during initial stage of culture; gradually lost luster Opaque Light scarlet |
| (2) Bouillon agar slant culture | Linear growth (with occasional formation of creases) Light scarlet Lustrous |

Table 3-continued

Bacteriological Properties

| Deposit No. | FERM-P No. 2891 |
|---|---|
| j | |
| (3) Bouillon agar stab culture | No change of medium Linear growth close to surface |
| (4) Bouillon gelatine stab culture | Linear growth close to surface without liquefaction |
| (5) Bouillon liquid stationary culture | Slight formation of film on surface Slight turbidity Sedimentation observed |
| (6) Litmus milk test | Slightly alkaline |
| [III] Physiological properties | |
| (1) Reduction of nitrate | + |
| (2) Denitrification | − |
| (3) MR test | − |
| (4) VP test | − |
| (5) Formation of indole | − |
| (6) Formation of hydrogen sulfide | + |
| (7) Hydrolysis of starch | − |
| (8) Utilization of citric acid using each of Koser medium and Christensen medium) | − |
| (9) Utilization of inorganic nitrogen sources (nitrates and ammonium salts) | + |
| (10) Formation of pigment | − |
| (11) Urease | − |
| (12) Oxidase | − |
| (13) Catalase | + |
| (14) Hydrolysis of sorbitan monooleate polyoxyethylene (available under trademark of "Tween 80") | + |
| (15) A) pH for growth | 4.5 − 9.0 |
| B) Optimum pH for growth | 5.5 − 7.0 |
| (16) A) Temperature for growth | 20 − 40° C |
| B) Optimum temperature for growth | 30 ± 3° C |
| (17) Behaviour to oxygen | Aerobic |
| (18) O-F test (by Hugh Leifson method) | |
| 1) L-arabinose | − |
| 2) D-xylose | − |
| 3) D-glucose | + |
| 4) D-mannose | − |
| 5) D-fructose | + |
| 6) D-galactose | − |
| 7) Maltose | − |
| 8) Sucrose | − |
| 9) Lactose | − |
| 10) D-trehalose | − |
| 11) D-sorbitol | + |
| 12) D-mannitol | + |
| 13) Inositol | − |
| 14) Glycerol | + |
| 15) Starch | − |
| | No gas production from any of the foregoing sugars observed. |
| (19) Assimilability of cis-epoxysuccinic | + |
| [IV] Source of isolation | Soil |

Note) In Table 2 and Table 3, the sign "+" means an affirmative result and the number of +'s increases with the increasing degree of the magnitude indicated and the sign "−" means a negative result. In Table 2, the sign "±" means that the result is such that definite rating of neither + nor − can be given.

A study of the foregoing bacteriological properties against the data of Bergey's Manual of Determinative Bacteriology, 8th ed., 1974 reveals that the three strains, FERM-P No. 2879, FERM-P No. 2880 and FERM-P No. 2881, have mutually similar bacteriological properties: They are invariably Gramnegative, aerobic, short-rod microorganisms. It is plain that they should be classified under Part 7 or Part 10 of said Manual. Further, the fact that the three strains are all observed to lack motility, to show no formation of spore, to give a negative result of catalase test and to oxidize ethanol to acetic acid and lactic acid to carbon dioxide at pH 4.5, the fact that they show fair growth at pH 4.5 and the fact that they are incapable of fermenting sugars and the fact that they produce acids from sugars all lead to a conclusion that they are bacteria belonging to the genus Acetobacter. However, it is noted that they clearly differ in cell size, assimilability of acetic acid, existence of no flagellum, oxidizability of alcohols, etc. from *Acetobacter pasteurianus* subsp paradoxus and *Acetobacter peroxidans* which are indicated in said Bergey's Manual to be catalase-negative acetobacters. In the light of these factors, the inventors have concluded that these three strains are to belong to new species and therefore have named them "*Acetobacter curtus.*" *Acetobacter curtus* No. 4, *Acetobacter curtus* No. 10 and *Acetobacter curtus* No. 21 exhibit virtually the same bacteriological properties and are barely observed to differ very slightly in terms of reducibility of nitrates, magnitude of urease activity, extent of production of acids from sugars, etc. They have, accordingly, decided to consider each of the three strains as relative species of each other.

A review of the morphological and physiological properties of FERM-P No. 2891 leads to a conclusion that the strain belongs to the genus Corynebacterium. The inventors, therefore, have named it "Corynebacterium S-13."

It is generally held that production of a cis-epoxysuccinic acid-hydrolase by the culture of a microorganism necessitates culturing the microorganism in a medium incorporating therein cis-epoxysuccinic acid or salts thereof (Japanese Patent Laid Open Nos. 140683/1975, 140684/1975 and 145586/1975). It has heretofore been held that said enzyme is hardly induced when the culture is carried out in a medium using as the carbon source only substances such as glucose, sucrose, alcohols and organic acids, etc. which can serve as effective carbon sources for microorganisms in general. The inventors have discovered the fact that tartaric acid is, unexpectedly, possessed of an ability to induce said enzyme similarly to cis-epoxysuccinic acid.

A typical method for the manufacture of a cis-epoxysuccinic acid-hydrolase is described below: This is a method for the manufacture of a cis-epoxysuccinic acid-hydrolase, which comprises the culturing step of a microorganism capable of assimilating cis-epoxysuccinic acid or salts thereof in a medium incorporating therein either tartaric acid or salts thereof, and the collecting step of the cis-epoxysuccinic acid-hydrolase thus produced from the product mixtures.

In this method, the tartaric acid or salts thereof which are incorporated in the culture medium serves not merely as the carbon source for the microorganism but also as an enzyme inducer.

The tartaric acid which is usable in this method is D-tartaric acid, L-tartaric acid, DL-tartaric acid, meso-tartaric acid or mixtures thereof. The salts of tartaric acid which are usable therein include metallic and non-metallic salts of the acid and substances containing such salts. The metallic moieties of said metallic salts are required not to inhibit the growth of said microorganism. Examples of the metals include alkali metals represented by sodium and potassium, alkaline earth metals represented by calcium and magnesium, etc. Examples of the bases in the non-metallic salts of tartaric acid are ammonium, amines, etc. The ammonium and amines additionally serve as the nitrogen source. Examples of the salts of tartaric acid, therefore, include sodium tartrate, potassium tartrate, magnesium tartrate, sodium potassium tartrate, sodium hydrogen tartrate, potassium hydrogen tartrate, calcium hydrogen tartrate, ammonium tartrate, ammonium hydrogen and ammonium potassium tartrate.

The amount in which the tartaric acid or salts thereof is added to the medium is such that the concentration thereof in the medium generally ranges from 0.1 to 10 percent by weight, preferably from 1.0 to 5.0 percent by weight. When the amount is such that the concentration fails to reach the lower limit of 0.1 percent by weight, the incorporation of that tartaric acid or salts thereof brings about substantially no effect. When the amount is such that the concentration exceeds the upper limit of 10 percent by weight, it inhibits the growth of the microorganism. The tartaric acid or salts thereof is incorporated in the medium at the time of either preparing the medium or starting the culture.

As the culture medium into which the tartaric acid or salts thereof is incorporated, any of culture media which are generally used for the culture of microorganisms will suffice. For example, the medium may contain a carbon source such as glucose, a nitrogen source such as ammonium ion, nitrate ion or urea, a phosphoric acid source such as potassium dihydrogen phosphate, a potassium source such as potassium chloride, a magnesium source such as magnesium sulfate, and traces of metal ions such as iron ion ($Fe^{++}$), manganese ion ($Mn^{++}$), cobalt ion ($Co^{++}$), molybdenum ion ($Mo^{++}$) or copper ion ($Cu^{++}$). It may furthermore contain organic micronutrient sources such as yeast extract, the hydrolysis product of casein by acid (available under the trademark "Casamino acid": Difco), peptone, meat extract, a vitamin or an amino acid in an ordinarily accepted proportion. It may contain an anti-foaming agent, a surface active agent, etc.

In the culture of the microorganism, the culturing temperature is generally in the range of 20° to 35° C, preferably in the range of 28° to 31° C and the pH value of the medium is generally in the range of 4.5 to 7.5, preferably in the range of 5.5 to 7.0. The culture is incubated aerobically. The growth of the microorganism reaches its stationary phase after two to five days. When the culture is carried out outside the tolerable range of culture conditions, the microorganism fails to obtain sufficient growth and, in the worst case, ends up in total destruction. When the pH value of the medium rises in consequence of gradual consumption of the tartaric acid or salts thereof, it is desirable to continue the culture while controlling the pH value by addition of an inorganic acid such as sulfuric acid or hydrochloric acid or an organic acid such as acetic acid.

This method has great commercial significance in that the cis-epoxysuccinic acid-hydrolase can be obtained by effectively utilizing DL-tartaric acid, for example, which occurs as a by-product in the chemical synthesis of cis-epoxysuccinic acid, the very compound constituting the substrate of cis-epoxysuccinic acid-hydrolase.

Desired induction of the enzyme can also be obtained by using *Acetobacter curtus* No. 4, *Acetobacter curtus* No. 10, *Acetobacter curtus* No. 21 or *Corynebacterium* S-13, etc. utilizing cis-epoxysuccinic acid or salts thereof as the substrate, similarly to tartaric acid or salts thereof.

A typical example of the method adopted for the manufacture of L(+)-tartaric acid or salts thereof by the enzymatic reaction involving the use of said cis-epoxysuccinic acid-hydrolase is described below.

As the raw material, not merely cis-epoxysuccinic acid but metallic salts or non-metallic salts of the acid or a substance containing said acid or salts may be used. Examples of the metallic moieties in said metallic salt of cis-epoxysuccinic acid include sodium, potassium, calcium, magnesium, iron, aluminum, zinc, manganese and cobalt which have no inhibitive action to the conventional enzymes. Examples of the base in said non-metallic salts of the acid include ammonium and amines. Concrete examples of the salts of cis-epoxysuccinic acid include disodium cis-epoxysuccinate, calcium cis-epoxysuccinate, sodium calcium cis-epoxysuccinate, potassium sodium cis-epoxysuccinate, calcium hydrogen cis-epoxysuccinate, and ammonium cis-epoxysuccinate.

A sample of cis-epoxysuccinic acid-hydrolase is added to the aqueous solution of the raw material or to the suspension of the raw material, with the resultant mixture adjusted to pH 4 to 10, preferably pH 7.5 to 8.5. The mixture is greatly agitated at temperatures below 65° C, desirably in the range of from 20° To 45° C, and preferably around 38° C. There is consequently obtained an enzymatic reaction mixture.

The development of the reaction can be followed by sampling the reaction mixture at required intervals and determining the cis-epoxysuccinic acid concentration. For the determination of the cis-epoxysuccinic acid concentration, there may be adopted a method which resorts to the reaction between hydrochloric acid and the epoxy group, for example.

The cis-epoxysuccinic acid-hydrolase sample may be suitably selected from among a culture broth, live microbic cell, dry microbic cell, gel entrapped microorganism, cell free extract, crude enzyme solution, purified enzyme, immobilized enzyme, etc.

In the method of the present invention, use of a gel entrapped microorganism is recommended. The method which proves advantageous for the entrapment of the aforementioned microorganisms comprises causing an acrylic acid amide type monomer to undergo polymerization in a liquid containing therein a microorganism capable of exhibiting an enzymatic activity of producibility of L(+)-tartaric acid or salts thereof.

A specific manner in which this method is accomplished is described below.

The microorganism which is possessed of the enzymatic activity of producibility of L(+)-tartaric acid or salts thereof is cultured by a method already known to the art. Although the form in which the microorganism possessed of the enzymatic activity of producibility of L(+)-tartaric acid or salts thereof is used is not specifically limited, said microorganism may be used in the form of live microbic cell, dry microbic cell, cell free extract or culture broth of microbic cell or a mixture thereof.

The microorganism possessed of the enzymatic activity of producibility of L(+)-tartaric acid or salts thereof is entrapped as it is enclosed with the three-dimensional reticular structure of a resin. To be more specific, said entrapment of the microorganism is accomplished by dissolving the acrylic acid amide type monomer in an aqueous medium such as water, an isotonic saline solution or a buffer solution which does not substantially inhibit the activity of the microorganism, then dispersing the microorganism in the resultant solution and initiating the polymerization reaction of the acrylic acid amide type monomer by addition thereto of a polymerization initiator and, as occasion demands, a polymerization accelerator. The ensuing polymerization reaction converts the reaction mixture substantially in its whole amount into an agar-like gel. The term "gel entrapped microorganism" as used in this invention shall mean the agar-like gel thus obtained and the microorganism enclosed therewith.

The content of the microorganism in the reaction mixture during the polymerization reaction, though variable with the kinds of the microorganism to be used and the form in which it is used, is generally in the range of 0.01 to 50 percent by weight, preferably in the range of 0.05 to 20 percent by weight. When the content fails to reach the lower limit of 0.01 percent by weight, there is a possibility that, as described herein below, the enzymatic reaction will not be obtained at a rate advantageous for practical use while the gel entrapped microorganism to be prepared consequently is utilized in the production of L(+)-tartaric acid or salts thereof. When the content exceeds the upper limit of 50 percent by weight, there may ensue a disadvantage that the gellation fails to proceed uniformly or a part of the microbic cell may escape entrapment with gel and flow out.

The acrylic acid amide type monomer which is used in the present polymerization reaction is a polymerizable monomer possessed of the atomic group of the formula, Examples of the monomer which is advantageously used herein include acrylic acid amide, N,N'-lower alkylene di(acrylic acid amide)s such as, for example, N,N'-methylene di(acrylic acid amide); N,N'-ethylene di(acrylic acid amide) and N,N'-propylene di(acrylic acid amide); N-(hydroxyalkyl) acrylic acid amides such as, for example, N-methylol acrylic acid amide; N-alkyl acrylic acid amides such as, for example, N,N-dimethyl acrylic acid amide; and di(acrylic acid amide) dialkyl ethers such as, for example, 1,1'-di(acrylic acid amide) dimethyl ether. Of these acrylic acid amide type monomers, particularly desirable for the intended use are acrylic acid amide and N,N'-lower alkylene di(acrylic acid amide)s. These acrylic acid amide type monomers may be used either singly or in the form of mixtures consisting of two or more members.

Although the concentration of the acrylic acid amide type monomer in the reaction mixture at the time of the polymerization reaction is variable with the particular kind of the monomer in use, it is only required to be such that at least the reaction mixture, upon polymerization, will undergo gellation. Generally, it is in the range of from 1 to 30 percent by weight and commercially preferably from 5 to 20 percent by weight.

Any polymerization initiator may be used insofar as it does not inhibit the enzymatic activity of the microorganism in use. Examples of the known polymerization initiator thus usable include salts of per acids such as ammonium persulfate, sodium persulfate and potassium persulfate and organic per acids such as peroxyformic acid and peroxyacetic acid.

Although the concentration of the polymerization initiator in the reaction mixture may be varied to a wide extent, the gellation proceeds advantageously when the concentration generally ranges from 0.01 to 1 percent by weight.

When there is used a polymerization accelerator at all, it is required to be of a type which does not inhibit the enzymatic activity of the microorganism. Examples of the known polymerization accelerator include β-dimethylaminopropionitrile and N,N,N',N'-tetramethyl ethylenediamine.

The range of the concentration of the polymerization accelerator in the reaction mixture is similar to that of the polymerization initiator.

The polymerization reaction may be allowed to proceed in the presence of an antibacterial agent in the reaction mixture. Where there is used an antibacterial agent at all, said antibacterial agent is only required to be of a type which does not inhibit the enzymatic activity of the microorganism but represses the growth of extraneous bacteria. Particularly desirable examples of the antibacterial agent are cationic surface active agents such as dodecyl pyridinium halides, halogenated benzalconiums and lauryl trimethylammonium halides, for they not only possess an antibacterial ability but also serve to enhance the permeability of the gel entrapped microorganism to be consequently obtained.

The concentration of the antibacterial agent in the reaction mixture, though not specifically limited, is generally desired to fall in the range of not more than 1000 ppm, preferably in the range of from 50 to 500 ppm. If the antibacterial agent is used in an amount corresponding to a concentration of more than 1000 ppm, there is derived no special advantage. Conversely, there may possibly be entailed a disadvantage that during the manufacture of L(+)-tartaric acid or salts thereof, the antibacterial agent will dissolve out and impair the purity of the product.

The polymerization reaction is carried out at temperatures of not more than 70° C, preferably in the range of from 20° to 50° C. The temperature of the polymerization is not desired to exceed the upper limit of 70° C, for the microorganism in use may possibly be inactivated at temperatures beyond this limit. Generally a period of 10 minutes to one hour will suffice as to the polymerization reaction, although it is variable with the kind of acrylic acid amide type monomer, that of the polymerization initiator and that of the polymerization accelerator to be used, their respective concentrations in the reaction mixture and the temperature of the polymerization reaction. The pH value of the reaction mixture at the time of the polymerization is in the range of from 4 to 10, preferably from 6 to 9. If the pH value of the reaction mixture is less than 4 or it exceeds 10, there may ensue a possibility that the microorganism in use will be deprived of its enzymatic activity.

The gel entrapped microorganism obtained as described above has the microorganism entrapped perfectly in the polymerized gel of acrylic acid amide. It can, therefore, be used continuously for a long time without experiencing disintegration of the gel coat and attendant outflow of the entrapped microorganism and degradation of the enzymatic activity. Most of all, the gel entrapped microorganism thus prepared enjoys a high enzymatic activity of producibility of L(+)-tartaric acid or salts thereof.

When the gel entrapped microorganism is brought into contact, in its crushed form or in its uncrushed form, with the aqueous solution of cis-epoxysuccinic acid or salts thereof, it causes an enzymatic reaction and produces L(+)-tartic acid of salts thereof. The gel entrapped microorganism is desired to have a particle diameter distribution in the range of from 5 mesh pass to 100 mesh stop (as measured by the method of JIS G 3555-1964). Examples of the cis-epoxysuccinate which is usable as the substrate in the enzymatic reaction include alkali metal salts such as the disodium salt, dipotassium salt, monosodium monopotassium salt, monosodium salts and monopotassium salts; alkaline earth metal salts such as magnesium salts, calcium salts and barium salts; and nitrogen-containing salts such as the diammonium salt, monoammonium salts, diamine salts and monoamine salts. Commercially it is desirable to use normal salts possessed of relatively higher solubility to water such as, for example, the disodium salt, dipotassium salt, monosodium monopotassium salt, magnesium salts, diammonium salt and diamine salts. Absolutely no limit is fixed as to the origin of cis-epoxysuccinic acid or salts thereof which is to be used in the enzymatic reaction. For example, cis-epoxysuccinic acid derivatives such as esters and acid amides which are readily hydrolyzed to produce cis-epoxysuccinic acid may be converted into the correpsonding cis-epoxysuccinic acid or salts thereof and, in that form, put to the enzymatic reaction. The reaction mixture containing cis-epoxysuccinic acid or salts thereof obtained by the reaction of hydrogen peroxide with maleic acid or salts thereof may similarly be used in its unaltered form or, as occasion demands, in its diluted form.

In producing L(+)-tartaric acid or salts thereof by using as the raw substrate mixture said reaction mixture containing cis-epoxysuccinic acid or salts thereof and obtained by the reaction of hydrogen peroxide with maleic acid or salts thereof, it is desired to use the gel entrapped microorganism which contain a microorganism possessed of substantially no catalase activity such as, for example, *Acetobacter curtus* No. 4, *Acetobacter curtus* No. 10 or *Acetobacter curtus* No. 21. If a microorganism possessed of catalase activity is used in this case, there is a possibility that the residual hydrogen peroxide in the reaction mixture containing cis-epoxysuccinic acid or salts thereof will be decomposed and the oxygen resulting from the decomposition of said hydrogen peroxide will interfere with the enzymatic reaction. If this gel entrapped microorganism is used in the form of the fixed-bed, even the slightest amount of oxygen bubbles may possibly clog the fine pores of the gel entrapped microorganism and consequently degrade the permeability.

No particular limit is fixed as to the concentration of the aqueous solution of cis-epoxysuccinic acid or salts thereof to be used in the enzymatic reaction. Even a highly diluted aqueous solution or a supersaturated aqueous solution can be used similarly effectively. In addition, the aqueous solution of cis-epoxysuccinic acid or salts thereof may have incorporated therein buffer agents so as to be used as a buffer solution. Otherwise, there may be incorporated therein sodium chloride or some other osmotic pressure-adjusting agents so as to be employed as a physiological isotonic solution. Omission of the use of such buffer agents or osmotic pressure-adjusting agents may possibly prove to be rather advantageous, depending on the particular purpose for which the end product is used. Suitable addition of antibacterial agents like the ones mentioned previously to the aqueous solution of cis-epoxysuccinic acid or salts thereof is all the more effective in obtaining the enzymatic reaction by use of the gel entrapped microorganism. The concentration in which the antibacterial agents are used is not specifically limited but is desired to be not more than 1000 ppm, preferably in the range of from 50 to 500 ppm. If the antibacterial agents are used at a concentration exceeding the upper limit of 1000 ppm, there is derived no special advantage. Conversely, such excess antibacterial agents may possible impair the purity of the produced L(+)-tartaric acid or salts thereof.

The aqeous solution of cis-epoxysuccinic acid or salts thereof which is used for the enzymatic reaction hereof is desired to be sterilized as by heating or filtration through a membrane prior to its actual use in said reaction.

When the enzymatic reaction is carried out by use of this gel entrapped microorganism, the conditions for the reaction are slightly eased as compared with the reaction effected by using cis-epoxysuccinic acid-hydrolase in any other forms. To be specific, the temperature of the enzymatic reaction is to range below 70° C, preferably in the range of from 20° to 50° C. If the temperature exceeds the upper limit of 70° C, there is a possibility that the gel-entrapped microorganism used in the enzymatic reaction will be deprived of its enzymatic activity. The pH value of the reaction mixture in the enzymatic reaction is desired to fall in the range of from 4 to 10, preferably from 6 to 9. If the pH value is less than 4 or it exceeds 10, then the gel entrapped microorganism to be used in the enzymatic reaction may possibly be deprived of its enzymatic activity. The contact time between the entrapped microorganism and the aqueous solution of cis-epoxysuccinic acid or salts thereof during the enzymatic reaction is generally in the range of 0.01 to 100 hours, although it is variable with the temperature, pH value, desired level of yield, etc.

The enzymatic reaction involving the use of said gel entrapped microorganism can be carried out by a batchwise method, a continuous method or a semi-continuous method, whichever may prove advantageous to the occasion.

In the batchwise method, an enzymatic reaction product mixture containing L(+)-tartaric acid or salts thereof can be obtained by mixing the aqueous solution of cis-epoxysuccinic acid or salts thereof with the gel entrapped microorganism, then, shaking or agitating the mixture and subsequently separating the gel entrapped microorganism from the resultant mixture by an ordinary solid-liquid separating technique such as centrifugation or filtration. The gel entrapped microorganism thus separated and recovered may be reused in the next cycle of enzymatic reaction.

As the continuous method, the so-called fixed-bed method is available which comprises allowing the aqueous solution of cis-epoxysuccinic acid or salts thereof to flow through a column packed with the gel entrapped microorganism.

As the semi-continuous method, there can be cited the so-called suspended-bed method which comprises continuously feeding the gel entrapped microorganism and the aqueous solution of cis-epoxysuccinic acid or salts thereof at the same time to a reaction tank, agitating the charge, withdrawing from the reaction tank the reaction mixture of an amount corresponding to the combined amount of the charge and separating and recovering the gel entrapped microorganism from the withdrawn reaction mixture as by the technique of decantation.

Thus, the product mixture of enzymatic reaction containing L(+)-tartaric acid or salts thereof can readily be obtained. The expression "product solution of enzymatic reaction" as used herein means the effluent from the column in the case of the continuous method of production and the solution remaining after the separation of the gel entrapped microorganism from the reaction mixture in the case of the batchwise or semi-continuous method. Depending on the condition of agitation, the individual particles of the gel entrapped microorganism may possibly collide into one another with violence sufficient to undergo disintegration. In consideration of this disadvantage, adoption of the fixed-bed method is desirable.

In the continuous method, the feed rate of cis-epoxysuccinic acid or salts thereof to the reaction column is from 0.1 to 15 g/hour in terms of free cis-epoxysuccinic acid per g of the microorganism contained in said gel entrapped microorganism, although it is variable with the enzymatic activity of said gel entrapped microorganism. It may be less than 0.1 g/hour or more than 15 g/hour. If it fails to reach the lower limit of 0.1 g/hour, however, the rate of formation of L(+)-tartaric acid or salts thereof is too low for the enzymatic reaction to be commercially practical. If it exceeds the upper limit of 15 g/hour, the concentration of L(+)-tartaric acid or salts thereof to be formed in the enzymatic reaction solution is very low as compared with that of the unaltered cis-epoxysuccinic acid or salts thereof, possibly rendering the refining operation difficult to accomplish.

For the collection of the produced L(+)-tartaric acid or salts thereof, there is employed a procedure which comprises, for example, adding the aqueous solution of calcium chloride, for example, to the product mixture of the enzymatic reaction or, as occasion demands, to the solution obtained by removing the enzyme sample used from said product mixture of enzymatic reaction for thereby inducing the precipitation of sparingly soluble or totally insoluble salts of L(+)-tartaric acid such as calcium L(+)-tartrate separating said salts by filtration, again suspending the salts in water and, while under agitation, adding dilute sulfuric acid, etc. thereto for thereby adjusting the pH value of the suspension to 1.8, removing from the suspension the precipitated sparingly soluble or totally insoluble salts such as calcium sulfate and finally removing the water content from the remaining liquid such as by, for example, reduced-pressure concentration to afford crude crystals of L(+)-tartaric acid. Required refining of the crude crystals is accomplished by dissolving the crude crystals in water, passing the aqueous solution through a column packed with a strongly acidic cation-exchange resin such as, for example, Amberlite IR 120 (H+ type cation-exchange resin made by Rohm and Haas Company) for thereby causing adsorption of the acid on the resin, eluting the adsorbed acid with water, again passing the eluate through a column packed with a strongly basic anion-exchange resin such as, for example, Amberlite IRA 400 (formic acid type anion-exchange resin made by Rohm and Haas Company) and eluting the adsorbed acid with 9N formic acid. Purified L(+)-tartaric acid is obtained by concentrating the resultant eluate.

By the present invention L(+)-tartaric acid or salts thereof which are important industrial materials can readily be produced in large quantities and high yields with high selectivity. Thus, this invention has an extremely high commercial value.

When the gel entrapped microorganism is used in the enzymatic reaction, the resultant reaction mixture is substantially free from such extraneous impurities as enzyme, microbic cell and other proteinaceous substances. By a simple aftertreatment, therefore, L(+)-tartaric acid or salts thereof possessed of high purity can be obtained in high yields from the enzymatic reaction solution.

In the case of the reaction involving the use of the gel entrapped microorganism, the production of L(+)-tartaric acid or salts thereof can be carried out continuously for a long time without requiring incorporation of buffer agents and/or osmotic pressure-adjusting agents to the aqueous solution of cis-epoxysuccinic acid or salts thereof being used as the raw material for the enzymatic reaction. The purity of the produced L(+)-tartaric acid or salts thereof is much higher when the enzymatic reaction is carried out without the use of said buffer agents and/or osmotic pressure-adjusting agents than otherwise.

Now, the present invention is described specifically hereinbelow with reference to its preferred embodiments. In Examples 38–42, the microorganism used was invariably *Acetobacter curtus* No. 21. When the same experiments were performed by using microorganisms other than *Acetobacter curtus* No. 21, namely *Acetobacter curtus* No. 4, *Acetobacter curtus* No. 10, etc., there were obtained similar results.

In Examples 38–42, the enzymatic activities of the cis-epoxysuccinic acid-hydrolase were determined by the following method: A prescribed amount of a given substance containing the cis-epoxysuccinic acid-hydrolase is added to the aqueous solution containing 1 percent by weight of disodium cis-epoxysuccinate and adjusted to pH 8.0 by addition of a phosphate buffer solution and then allowed to react on said salt at 34° C for one hour. At the end of this reaction, the reaction solution is boiled for five minutes to stop the reaction. If the reaction solution happens to contain therein microbic cell or other similar insoluble matter, it is centrifuged to separate said impurities and consequently obtain a clear supernatant. This supernatant is tested for angle of rotation. By applying the found angle of rotation to the calibration curve prepared in advance showing the content of disodium L(+)-tartrate as the function of the angle of rotation, the amount of disodium L(30 )-tartrate produced by said reaction is calculated. The enzymatic activity of enzyme is expressed by the amount of the disodium L(+)-tartrate produced per ml of the given substance containing the cis-epoxysuccinic acid-hydrolase per hour, with $\mu.mol/hr/ml$ used as the denomination.

In Examples 1–55, whenever the "parts" and "%" are used, they mean "parts by weight" and "percent by weight", respectively, unless otherwise specified. The 0.1M phosphate buffer solution (pH 8.0), 0.05M phosphate buffer solution (pH 8.0) and 0.25M phosphate buffer solution (pH 8.0) indicated in Examples 43–55 mean the buffer solutions obtained by diluting with water respectively to two times, four times and eight times the original volume, the mixture of 5.3 parts by volume of an aqueous 0.2M dihydrogen monosodium phosphate solution with 94.7 parts by volume of an aqueous 0.2M monohydrogen disodium phosphate solution. The mesh scale used in Examples 43–55 to indicate the particle diameter is in accordance with JIS G 3555-1964.

EXAMPLE 1

In a 100-ml portion of a culture medium containing 0.5 percent of dipotassium phosphate, 0.2 percent monopotassium phosphate, 0.3 percent of ammonium sulfate, 0.05 percent of heptahydrated magnesium sulfate, 0.001 percent of heptahydrated ferrous sulfate, 0.01 percent of yeast extract and 1.0 percent of disodium cis-epoxysuccinate and adjusted in pH 6.5, the strain of *Acetobacter curtus* No. 4 (FERM-P No. 2879) was inoculated and cultured at 30° C for 24 to 48 hours. The disodium cis-epoxysuccinate present in the culture broth was wholly consumed to produce 0.45 g of sodium L(+)-tartrate (yield 40 percent based on disodium cis-epoxysuccinate). The reaction mixture was centrifuged to separate the microbic cells and to obtain a supernatant. By adding to this supernatant about 25 ml of an aqueous calcium chloride having a concentration of 0.1 mol/l, there was obtained a precipitate of calcium L(+)-tartrate. The precipitate was separated by filtration and again suspended in about 50 ml of water. While the suspension was kept under agitation, 0.1N sulfuric acid was added thereto until the pH of the suspension became 1.8. The produced precipitate of calcium sulfate was separated by filtration. The filtrate was concentrated to dryness under reduced pressure to afford about 0.28 g of L(+)-tartaric acid in the form of crystals. The L(+)-tartaric acid thus obtained was found to have a specific rotatory power of $[\alpha]_D^{30} = +15.5°$ (10 percent in concentration). Comparison of the results with those of the extra pure reagent grade L(+)-tartaric acid available on the market revealed the present product to have an optical purity of 100 percent.

EXAMPLE 2

To the culture broth obtained in Example 1, 1.0 g of disodium cis-epoxysuccinate was added. The culture broth was adjusted to pH 8.0 and shaken at 35° C for four hours. The newly added substrate was used up and the culture broth was found to contain 1.29 g of sodium L(+)-tartrate (59 percent of yield of sodium L(+)-tartrate based on the whole substrate charged, 78 percent of yield of sodium L(+)-tartrate based on the newly incorporated substrate). In this manner, 1.0 g portions of disodium cis-epoxysuccinate were added one after another to a total of 20.0 g. Finally, the substrate thus successively added was wholly used up and the culture broth was found to contain 2.18 g of sodium L(+)-tartrate (89 percent of yield of sodium L(+)-tartrate based on the whole substrate charged). The culture broth was centrifuged to afford a supernatant. By adding to the supernatant about 120 ml of a calcium chloride solution having a concentration of 1 mol/l, there was obtained the precipitate of calcium L(+)-tartrate. The precipitate was separated by filtration and suspended in about 200 ml of water. While the suspension was kept under agitation, 1N sulfuric acid was added until the pH value of the suspension became 1.8. The precipitate of calcium sulfate thus produced was separated by filtration. The filtrate was concentrated to dryness under reduced pressure to afford 14.7 g of L(+)-tartaric acid in the form of crystals. The crude crystals thus obtained were dissolved in water. The aqueous solution was passed through a column measuring 3 × 80 cm and packed with Amberlite IR 120 (H+ type cation-exchange resin) and the adsorbate was eluted with about 1000 ml of water. The resultant eluate was passed through another column measuring 3 × 80 cm and packed with Amberlite IRA 400 (formic acid type anion-exchange resin) and the adsorbate was eluted with about 1000 ml of 9N formic acid. The eluate thus obtained was concentrated to dryness under reduced pressure to afford 13.5 g of pure tartaric acid. The L(+)-tartaric acid thus produced was found to have an optical purity of 100 percent.

EXAMPLE 3

The culture broth obtained similarly to Example 1 was centrifuged to separate the cells therefrom. The cells were suspended in 200 ml of a 0.05 mol/l phosphate buffer solution adjusted in advance to pH 7.0 and the suspension was again centrifuged to clean the cells. This cleaning was repeated to give a total of three cycles. A 0.5 g portion of the cleaned cells was added to a 100 ml of solution containing 1.0 g of dihydrated calcium hydrogen cis-epoxysuccinate and 0.3 g of calcium carbonate as the substrate. The resultant mixture was adjusted to pH 8.0 and shaken at 35° C for 4 hours. The substrate was wholly used up and the reaction mixture was found to have produced calcium L(+)-tartrate. The amount of calcium L(+)-tartrate thus produced was 1.09 g. The yield was 98%. The resultant reaction mixture was incorporated with both 1.0 g of dihydrated calcium hydrogen cis-epoxysuccinate and 0.3 g of calcium carbonate thereto and was shaken at 35° C for 4 hours. The substrate present in the reaction mixture was wholly used up and converted into calcium L(+)-tartrate. The amount of the product was 2.18 g and the yield thereof based on the charged substrate was 98%. In this manner, 1.0 g portions of dihydrated calcium hydrogen cis-epoxysuccinate and 0.3 portions of calcium carbonate were added one each at a time to respective totals of 20.0 g and 6.0 g. Finally, the substrate thus successively added was wholly used up to produce the precipitate of calcium L(+)-tartrate. The amount of the product thus produced was 22.0 g and the yield thereof was 99 percent. The calcium L(+)-tartrate was suspended in about 200 ml of water. While the suspension was kept under agitation, 1N hydrochloric acid was added until the precipitate of calcium L(+)-tartrate was dissolved. The resultant liquid was centrifuged to remove the microbic cells therefrom. The remaining solution was passed through a column measuring 3 × 80 cm and packed with Amberlite IR 120 (H+ type cation-exchange resin) and the adsorbate was eluted with water. By concentrating to dryness the eluate under reduced pressure, there was obtained 15.7 g of L(+)-tartaric acid in the form of crystals. The yield was 89 percent and the optical purity was 100 percent.

EXAMPLE 4

In a culture medium similar in composition to that of Example 1, except for the additional incorporation of 1.0 percent of disodium cis-epoxysuccinate and 1.0 percent of glucose as the carbon source, the strain of *Acetobacter curtus* No. 10 (FERM-P No. 2880) was inoculated and cultured at 30° C for 24 to 48 hours. From the resultant culture broth, the live microbic cells were removed by centrifugation. The cells were washed with a phosphate buffer solution having a concentration of 0.05 mol/l and a pH value of 7.0, then suspended in water and lyophilized. A 0.1 g portion of the lyophilized cells was gently shaken at 35° C for 4 hours in a 100 ml of a solution containing as the substrate 1.0 g of dihydrated calcium hydrogen cis-epoxysuccinate and having the pH value thereof adjusted to 8.0 with a sodium hydroxide solution. The substrate was wholly used up to produce sodium L(+)-tartrate and calcium L(+)-tartrate. From this point onward, the similar procedure as to Example 3 was repeated. The cell free culture liquid was passed through a column packed with the ion-exchange resin. The eluate was concentrated to dryness to afford 0.85 g of L(+)-tartaric acid.

The yield was 96 percent and the optical purity was 98 percent.

EXAMPLE 5

Clean microbic cells obtained similarly to Example 3 were placed in 100 ml of an aqueous solution containing as the substrate 1.0 g of cis-epoxysuccinic acid and having the pH value thereof adjusted to 8.0 with an aqueous sodium hydroxide solution and agitated at 35° C for four hours. The substrate was wholly used up to produce 1.40 g of sodium L(+)-tartrate. The yield was 95 percent. The reaction mixture was treated by following the procedure of Example 2. The L(+)-tartaric acid consequently obtained was found to have an optical purity of 100 percent.

EXAMPLE 6

The experiment of Example 5 was carried out by following the same procedure, except 1.0 g of disodium cis-epoxysuccinate was used as the substrate. The substrate was wholly used up to produce disodium L(+)-tartrate. The amount of the disodium L(+)-tartrate thus produced was 1.08 g and the yield was 98 percent. The L(+)-tartaric acid obtained by following the similar procedure as to Example 2 had an optical purity of 100 percent.

EXAMPLE 7

The experiment of Example 1 was repeated by following the same procedure, except the strain of *Acetobacter curtus* No. 21 (FERM-P No. 2881) was used in place of the strain of *Acetobacter curtus* No. 4. From the culture broth, clean microbic cells were obtained by following the procedure of Example 3. The clean cells were suspended in about 30 ml of acetone and then subjected to centrifugation. This cleaning of the cells with acetone was repeated to give a total of three cycles. The clean cell was dried at a temperature of not more than 30° C under reduced pressure to afford acetone-dried microbic cells. The treatment of Example 5 was repeated by following the same procedure, except 0.1 g of the acetone-dried cells were used and 1.0 g of sodium calcium cis-epoxysuccinate was used as the substrate. The substrate in the mixture was wholly used up to produce sodium L(+)-tartrate and calcium L(+)-tartrate. The amount of sodium L(+)-tartrate was 0.49 g and that of calcium L(+)-tartrate was 0.48 g and the combined yield was 97 percent. The L(+)-tartaric acid obtained by following the procedure of Example 3 was found to have an optical purity of 100 percent.

EXAMPLE 8

A 0.5 g portion of clean cells of *Acetobacter curtus* No. 21 (FERM-P No. 2881) obtained by following the procedure of Example 7 was gently shaken at 35° C for 4 hours in 100 ml of a solution containing as the substrate 1.0 g of diammonium cis-epoxysuccinate and adjusted in advance to pH 8.0 with aqueous ammonia. The substrate in the reaction mixture was wholly used up to produce 1.05 g of ammonium tartrate. The yield was 95 percent. The reaction mixture was centrifuged to remove microbic cells therefrom. The remaining solution, upon addition thereto of 0.6 of calcium carbonate, produced a precipitate of calcium L(+)-tartrate. The precipitate was separated by filtration and subjected to the treatment similar to that of Example 1. The L(+)-tartaric acid consequently obtained was found to have an optical purity of 100 percent.

EXAMPLE 9

Clean microbic cells of *Acetobacter curtus* No. 4 (FERM-P No. 2879) obtained by following the procedure of Example 3 were suspended in 100 ml of a 0.05 mol/l phosphate buffer solution (pH 7.0) and the suspension was treated by a cell breaker (Vibrogen Cellmill made by Edmond Wooler of West Germany) to obtain a homogenate. By centrifuging the resultant homogenate, there was obtained a soluble fraction, which was dialyzed with running water. The liquid obtained within the dialyzer was concentrated to 50 ml, which was used as the cell free extract. This cell free extract was adjusted to pH 8.0 by addition thereto of 1.0 g of tetrahydrated calcium cis-epoxysuccinate and then diluted with water to a total volume of 100 ml. The mixture thus obtained was shaken at 35° C for four hours. The substrate in the reaction mixture was wholly used up to produce calcium L(+)-tartrate. The amount of calcium L(+)-tartrate thus produced was 0.77 g and the yield was 99 percent. The calcium L(+)-tartrate was separated by filtration and then treated by following the procedure of Example 1 to obtain L(+)-tartaric acid. The L(+)-tartaric acid was found to have an optical purity of 100 percent.

EXAMPLE 10

Clean microbic cells of *Acetobacter curtus* No. 10 (FERM-P No. 2880) obtained by following the procedure of Example 4 were subjected to homogenization in the same way as in Example 9 to afford a soluble dialyzate. The dialyzate was fractionated with ammonium sulfate and the fraction of 0 to 0.5 saturation was collected. This ammonium sulfate fraction was dialyzed against a 0.05 mol/l phosphate buffer solution (pH 7.0) and the liquid obtained inside the dialyzer was concentrated to 30 ml, which was taken as crude enzyme liquid. To this crude enzyme liquid, an aqueous solution containing as the substrate 1.0 g of dihydrated calcium hydrogen cis-epoxysuccinate and 0.3 g of calcium carbonate was added. The resultant mixture was adjusted to pH 8.0 and then diluted with water to a total volume of 100 ml. The mixture thus obtained was shaken at 35° C for 4 hours. The substrate in the reaction mixture was wholly used up to produce calcium L(+)-tartrate. The amount of calcium L(+)-tartrate thus obtained was 1.09 g and the yield was 98 percent. The L(+)-tartaric acid obtained by following the procedure of Example 1 was found to have an optical purity of 100 percent.

EXAMPLE 11

In 100 ml of a solution containing as the substrate 5.0 g of disodium cis-epoxysuccinate, a 0.5 g portion of clean cells of *Acetobacter curtus* No. 10 (FERM-P No. 2880) prepared by following the procedure of Example 4 was shaken at pH 8.0 at 35° C for 15 hours. The substrate in the solution was wholly used up to produce sodium L(+)-tartrate. The amount of the sodium L(+)-tartrate thus obtained was 5.4 g and the yield was 98 percent. The L(+)-tartaric acid obtained by following the similar procedure to Example 1 was found to have an optical purity of 100 percent.

EXAMPLE 12

In a 200 ml portion of a culture medium having the same composition as that of Example 1, the strain of *Acetobacter curtus* No. 21 (FERM-P No. 2881) was inoculated and then treated by following the procedure of Example 7 to afford clean microbic cells. In 100 ml of a solution containing as the substrate 5.0 g of tetrahydrated calcium cis-epoxysuccinate, said clean cells were shaken at pH 8.0 at 35° C for eight hours. The substrate in the reaction mixture was wholly used up to produce calcium L(+)-tartrate. The amount of the product thus obtained was 0.75 g and the yield was 97 percent. The L(+)-tartaric acid obtained by following the similar procedure to Example 1 was found to have an optical purity of 100 percent.

EXAMPLE 13

The procedure of Example 12 was faithfully repeated, except the volume of the culture medium was increased to 400 ml. In 100 ml of an aqueous solution containing as the substrate 20.0 g of disodium cis-epoxysuccinate and adjusted to pH 8.0, the clean cells thus prepared were shaken at 35° C for 18 hours. The substrate in the reaction mixture was wholly used up to produce 20.9 g of sodium L(+)-tartrate. The yield was 95 percent. The L(+)-tartaric acid obtained by following the similar procedure to Example 1 was found to have an optical purity of 100 percent.

EXAMPLE 14

By following the procedure of Example 13 except for incorporation of 20.0 g of sodium ammonium cis-epoxysuccinate as the substrate, there was continued a total of 18 hours of enzymatic reaction. The substrate in the reaction mixture was wholly used up to produce 20.8 g of sodium ammonium L(+)-tartrate. The yield was 94 percent. The L(+)-tartaric acid obtained by following the procedure of Example 8 was found to have an optical purity of 100 percent.

EXAMPLE 15

Under the same conditions as in Example 13 except for use of clean sells which were cultured in 1 liter of the culture medium, the enzymatic reaction was continued for six hours. In the reaction mixture, 20.0 g of disodium cis-epoxysuccinate added thereto as the substrate was wholly used up to produce 21.4 g of sodium L(+)-tartrate. The yield was 97%. The L(+)-tartaric acid obtained by following the similar procedure to Example 1 was found to have an optical purity of 100 percent.

EXAMPLE 16

In 100 ml of a culture medium containing 0.3 percent of dipotassium phosphate, 0.1 percent of monopotassium phosphate, 0.1 percent of ammonium nitrate, 0.05 percent of heptahydrated magnesium sulfate, 0.001 percent of heptahydrated ferrous sulfate, 0.01 percent of yeast extract, and 1.0 percent of disodium cis-epoxysuccinate and adjusted to pH value of 7.0, the strain of Corynebacterium S-13 (FERM-P No. 2891) was inoculated and cultured at 30° C for 24 to 48 hours. The substrate, sodium cis-epoxysuccinate, in the culture broth was wholly used up and the broth was found to contain about 0.04 g of sodium L(+)-tartrate produced consequently. The yield was 3%.

EXAMPLE 17–20

Clean microbic cells of *Acetobacter curtus* No. 4 (FERM-P No. 2879) were obtained by following the procedure of Example 3. Aliquots, each of 0.5 g, of said clean cells were each added to 100 ml of an aqueous solution containing as the substrate 1.0 g of cis-epoxysuccinic acid and adjusted to a different pH value with sodium hydroxide and shaken at 35° C for a different length of time. In each reaction mixture, the substrate was wholly used up to produce sodium L(+)-tartrate. The amounts of sodium L(+)-tartrate produced and the respective yields thereof are shown in Table 4 in conjunction with the reaction conditions. In each test run, the L(+)-tartaric acid obtained by following the similar procedure to Example 1 was found invariably to have an optical purity of 100 percent.

Table 4

| Example No. | pH | Reaction time (hours) | Sodium L(+)-tartrate Amount produced | Yield | Optical purity of L(+) tartaric acid |
|---|---|---|---|---|---|
| Example 17 | 6.0 | 8.0 | 1.32g | 90% | 100% |
| Example 18 | 7.0 | 5.0 | 1.37 | 93 | 100 |
| Example 19 | 9.0 | 5.0 | 1.35 | 92 | 100 |
| Example 20 | 10.0 | 8.0 | 1.30 | 89 | 100 |
| Example 5 | 8.0 | 4.0 | 1.40 | 95 | 100 |

EXAMPLE 21–24

Clean microbic cells were obtained by following the procedure of Example 7, except for use of *Acetobacter curtus* No. 21 (FERM-P No. 2881) in place of *Acetobacter curtus* No. 4 (FERM-P No. 2879). Aliquots, each of 0.5 g, of said clean cells were each added to 100 ml of an aqueous solution containing as the substrate 1.0 g of disodium cis-epoxysuccinate and adjusted to pH 8.0 with sodium hydroxide and shaken at a different temperature for a different length of time. In each reaction mixture, sodium L(+)-tartrate was produced. The amounts of the sodium L(+)-tartrate thus produced and the corresponding yields are shown in Table 5 in conjunction with reaction conditions (temperature and time). In each test run, the L(+)-tartaric acid obtained by following the similar procedure to Example 1 was found to have an optical purity of 100 percent.

Table 5

| Example No. | Temperature (° C) | Reaction time (hours) | Sodium L(+)-tartrate Amount produced | yield | Optical purity of L(+)-tartaric acid |
|---|---|---|---|---|---|
| Example 21 | 18 | 10.0 | 1.06g | 96% | 100% |
| Example 22 | 24 | 7.0 | 1.05 | 95 | 100 |
| Example 23 | 29 | 6.0 | 1.02 | 93 | 100 |
| Example 24 | 39 | 4.0 | 0.98 | 89 | 100 |
| Example 6 | 35 | 4.0 | 1.08 | 98 | 100 |

EXAMPLE 25

In 100 ml of a solution containing 1.0 g of cis-epoxysuccinic acid and 1.43 g of an aqueous 33% methylamine solution and adjusted to pH value of 8.0, 0.5 g portion of clean microbic cells of *Acetobacter curtus* No. 10 (FERM-P No. 2880) prepared by following the procedure of Example 4 was added and shaken at 30° C for 6 hours. The reaction mixture was found to contain 1.32 g of di(methylamine) L(+)-tartrate produced consequently. The yield was 90 percent. This salt was converted to calcium L(+)-tartrate by addition of a solution of calcium chloride in the same manner as in Example 1, from which L(+)-tartaric acid was derived. The optical purity of the produced L(+)-tartaric acid was 100 percent.

salt of L(+)-tartaric acid, L(+)-tartaric acid was produced by following the procedure of Example 27. The optical purities found for the products are also shown in the table.

Table 6

| Example No. | Metal hydroxide, carbonate, etc. Specific compound | Weight (g) | pH | Temperature (° C) | Reaction time (hr) | Reacton product Specific product | Amount produced (g) | Yield (%) | Optical purity of L(+)-tartaric acid(%) |
|---|---|---|---|---|---|---|---|---|---|
| Example 28 | Calcium hydroxide | 0.56 | 7.5 | 35 | 4 | Calcium L(+)-tartrate | 1.40 | 98 | 100 |
| Example 29 | Barium carbonate | 1.50 | 7.0 | 35 | 6 | Barium L(+)-tartrate | 2.01 | 93 | 100 |
| Example 30 | Zinc hydroxide | 0.75 | 6.0 | 35 | 12 | Zinc L(+)-tartrate | 1.45 | 90 | 100 |
| Example 31 | Iron hydroxide | 0.54 | 6.0 | 35 | 18 | Iron L(+)-tartrate | 1.25 | 89 | 98 |
| Example 32 | Aluminum hydroxide | 0.39 | 6.0 | 35 | 10 | Aluminum L(+)-tartrate | 1.15 | 91 | 100 |
| Example 33 | Sodium carbonate | 0.80 | 8.0 | 32 | 5 | Sodium L(+)-tartrate | 1.43 | 97 | 100 |
| Example 34 | Potassium carbonate | 1.05 | 8.5 | 34 | 5 | Potassium L(+)-tartrate | 1.66 | 97 | 100 |
| Example 35 | Calcium oxide | 0.43 | 8.0 | 35 | 4 | Calcium L(+)-tartrate | 1.37 | 96 | 100 |
| Example 36 | Magnesium oxide | 0.31 | 8.0 | 35 | 5 | Magnesium L(+)-tartrate | 1.20 | 92 | 100 |

EXAMPLE 26

The experiment of Example 5 was carried out by following the same procedure except for using an aqueous solution of potassium hydroxide in the place of the aqueous solution of sodium hydroxide. The substrate in the reaction mixture was wholly used up to produce potassium L(+)-tartrate. The amount of the product thus obtained was 1.61 g and the yield was 94 percent. Similarly to the sodium L(+)-tartrate of Example 1, this potassium L(+)-tartrate was treated to afford L(+)-tartaric acid. This acid was found to have an optical purity of 100 percent.

EXAMPLE 27

In 100 ml of an aqueous solution containing 1.0 g of cis-epoxysuccinic acid and 0.44 g of magnesium hydroxide and adjusted to pH value of 8.0, a 0.5 g portion of clean microbic cells of *Acetobacter curtus* No. 4 (FERM-P No. 2879) obtained by following the procedure of Example 3 was added and shaken at 35° C for 5 hours. In the reaction mixture, there was formed magnesium L(+)-tartrate. The amount of the salt thus produced was 1.19 g and the yield was 91 percent. By treating this product with a column packed with Amberlite IR 120 (H+ type cation-exchange resin) similarly to Example 3, there was obtained L(+)-tartaric acid. This L(+)-tartaric acid was found to have an optical purity of 100 percent.

EXAMPLES 28–36

Aliquots, each 0.5 g, of clean microbic cells of *Acetobacter curtus* No. 4 (FERM-P No. 2879) prepared by following the procedure of Example 3, were each added to 100 ml of a solution containing 1.0 g of cis-epoxysuccinic acid and a varying metal hydroxide, metal oxide or carbonate and shaken at a different temperature for a different length of time. In each reaction mixture, a metal salt of L(+)-tartaric acid corresponding to said metal hydroxide, etc. was formed consequently. The amounts of the salts produced and their respective yields are shown in Table 6 in conjunction with the corresponding reaction conditions. From each metal

EXAMPLE 37

The procedure of Example 25 was repeated, except 1.53 g of triethylamine was used in place of an aqueous 33% methylamine solution. In the reaction mixture, 1.73 g of di(triethylamine) L(+)-tartrate was formed. The yield was 91 percent. The optical purity of the L(+)-tartaric acid obtained by repeating the procedure of Example 25 was found to be 100 percent.

EXAMPLE 38

In tap water, 2 g of disodium DL-tartrate, 0.2 g of $KH_2PO_4$, 0.1 g of $K_2HPO_4$, 0.3 g of $NH_4NO_3$, 0.05 g of $MgSO_4.7H_2O$, 0.05 g of yeast extract, 0.002 g of $FeSO_4.7H_2O$ and 0.001 g of $MnCl_2.4H_2O$ were dissolved to a total volume of 100 ml to be used as the culture medium. In this medium, the strain of *Acetobacter curtus* No. 21 (FERM-P No. 2881) was cultured by shaking at 30° C for 4 days. The initial pH value of the culture medium was 6.2. At the end of the culture, the culture broth was tested for enzymatic activity, which was shown to be 24 $\mu$.mol/hr/ml.

Comparative Example 1

By repeating the procedure of Example 38 except for use of 2 g of glucose in place of 2 g of disodium DL-tartrate, the strain of *Acetobacter curtus* No. 21 (FERM-P No. 2881) was cultured. When the culture broth was tested for enzymatic activity, it was shown to be almost nil.

EXAMPLE 39

The strain of *Acetobacter curtus* No. 21 (FERM-P No. 2881) was cultured by following the procedure of Example 38 except for use of 2 g of calcium DL-tartrate in place of 2 g of disodium DL-tartrate. The initial pH value of the culture medium in this case was 6.0. At the end of the culture, the culture broth was subjected to low-speed centrifugation at 500G in a centrifugal separator. Consequently, there was obtained a mixture containing the microbic cells and freed of insoluble calcium salts. This mixture was tested for enzymatic activity, which was shown to be 11 μ.mol/hr/ml.

EXAMPLE 40

With tap water, 20 g of disodium DL-tartrate, 2 g of $KH_2PO_4$, 1 g of $K_2HPO_4$, 3 g of $NH_4NO_3$, 0.5 g of $MgSO_4.7H_2O$, 0.5 g of yeast extract, 0.02 g of $FeSO_4.7H_2O$ and 0.01 g of $MnCl_2.4H_2O$ were dissolved to a total volume of 1000 ml to be used as the culture medium. In this culture medium, the strain of *Acetobacter curtus* No. 21 (FERM-P No. 2881) was aerobically cultured by using a jar fermentor. The volume of air supplied to the culture broth was 0.5 VVM, the temperature was kept at 30° C, and the pH value during the culture was maintained at 6.3 by use of an aqueous 10 percent by volume sulfuric acid solution. The culture was continued for 3 days. The culture broth thus produced was tested for enzymatic activity, which was shown to be 38 μ.mol/hr/ml. A 300-ml portion of this culture broth was centrifuged to separate microbic cells therefrom. The cells were dispersed in 50 ml of water. The resultant dispersion was mixed with 50 ml of an aqueous 20% disodium cis-epoxysuccinate having a pH value of 8.0 and the resultant mixture was held at 34° C for 10 hours to effect hydrolysis of said disodium cis-epoxysuccinate. At the end of the reaction, the reaction mixture was centrifuged. The supernatant was concentrated to dryness and refined to afford 11.3 g of dihydrated disodium L(+)-tartrate in the form of crystals. The optical purity of the crystals was found to be 97 percent based on the optical purity of the extra pure grade dihydrated disodium L(+)-tartrate available on the market. The X-ray diffraction spectrum and the IR spectrum obtained of the crystals were in perfect agreement with the corresponding spectra of the extra pure grade dihydrated disodium L(+)-tartrate available on the market.

EXAMPLE 41

With tap water, 30 g of disodium L(+)-tartrate, 5 g of glucose, 2 g of $KH_2PO_4$, 1 g of $K_2HPO_4$, 3 g of $(NH_4)_2SO_4$ and 0.5 g of $MgSO_4.7H_2O$ were dissolved to a total volume of 1000 ml to be used as the culture medium. In this medium, the strain of *Acetobacter curtus* No. 21 (FERM-P No. 2881) was cultured by following the procedure of Example 40. The culture broth was found to have an enzymatic activity of 56 μ.mol/hr/ml.

EXAMPLE 42

With tap water, 20 g of diammonium DL-tartrate, 2 g of $KH_2PO_4$, 1 g of $K_2HPO_4$, 0.5 g of $MgSO_4.7H_2O$ and 0.5 g of yeast extract were dissolved to a total volume of 1000 ml to be used as the culture medium. In this culture medium, the strain of *Acetobacter curtus* No. 21 (FERM-P No. 2881) was aerobically cultured by using a jar fermentor, with the feed volume of air fixed at 0.5 VVM, the temperature was maintained at 30° C and the pH value was controlled during the culture to 6.3 by use of an aqueous 10 percent by volume sulfuric acid solution. At the end of three days of culture, the culture broth was tested for enzymatic activity, which was shown to be 40 μ.mol/hr/ml.

EXAMPLE 43

In 100 parts of a liquid culture medium containing 0.5 percent of dipotassium monohydrogen phosphate, 0.2 percent of monopotassium dihydrogen phosphate, 0.3 percent of ammonium sulfate, 0.05 percent of heptahydrated magnesium sulfate, 0.001 percent of heptahydrated ferrous sulfate, 0.01 percent of yeast extract and 1.0 percent of disodium cis-epoxysuccinate and having a pH value of 6.5, the strain of *Acetobacter curtus* No. 21 (FERM-P No. 2881) was inoculated and cultured at 30° C for 48 hours. The resultant culture broth was centrifuged to separate the microbic cells therefrom. The separated cells were suspended in a 0.1M phosphate buffer solution (pH 7.0) and again centrifuged to have the cells washed. Said 0.1M phosphate buffer solution (pH 7.0) was obtained by diluting with water to twice the original volume, a mixture of an aqueous 0.2M monosodium dihydrogen phosphate solution with an aqueous 0.2M disodium monohydrogen phosphate solution at a voluminal ratio of 39/61.

To 1 part of the cell suspension containing 1.5 percent of cells, 6 parts of 0.1M phosphate buffer solution (pH 8.0), 0.75 part of acrylic acid amide, 0.04 part of N,N'-methylene di(acrylic acid amide), 0.5 part of an aqueous 2.5 percent potassium persulfate solution and 0.5 part of an aqueous 5 percent β-dimethylaminopropionitrile solution were added and allowed to polymerize at 30° C for 30 minutes. The polymer gel consequently obtained was crushed and the portion of the crushed gel particles falling in the particle diameter range of 6 mesh pass to 20 mesh stop which accounted for 90 weight percent of the whole gel was washed with a 0.1M phosphate buffer solution (pH 8.0) to obtain 9 parts of a gel entrapped microorganism.

Nine (9) parts of the gel entrapped microorganism was mixed with 10 parts of an aqueous 2 percent disodium cis-epoxysuccinate solution and, while under agitation, held at 30° C for 2 hours to have the microorganism reacted upon said salt. At the end of the reaction, the enzymatic reaction mixture was filtered to separate the gel entrapped microorganism. The filtrate was tested for rotatory power to determine the amount of disodium L(+)-tartrate formed by the reaction.

For the purpose of comparison, one part of the cell suspension similar to that described above was agitated with 10 parts of an aqueous 2 percent disodium cis-epoxysuccinate solution (pH 8.0) at 30° C for 2 hours to effect the reaction aimed at. At the end of the reaction, the reaction mixture was tested as described above to determine the amount of disodium L(+)-tartrate produced in consequence of the reaction.

From the results obtained above, the activity yield of the gel entrapped microorganism was found to be 74.0 percent.

The activity yield to be mentioned hereinbelow is defined as follows:

Activity Yield (%) = 
$$\frac{\text{Amount of disodium L(+) -tartrate formed by the gel entrapped microorganism}}{\text{Amount of disodium L(+)-tartrate formed by the same microorganism not in an entrapped form with gel}} \times 100$$

EXAMPLE 44

To 20 parts of a cell suspension obtained by following the procedure of Example 43, 3.75 parts of acrylic acid amide, 0.2 part of N,N'-methylene di(acrylic acid amide), 2.5 parts of an aqueous 2.5 percent potassium persulfate solution, 2.5 parts of an aqueous 5 percent β-dimethylaminopropionitrile solution and 15 parts of a 0.1N phosphate buffer solution (pH 8.0) were added and allowed to polymerize at normal room temperature for 30 minutes. The polymer gel thus produced was crushed and the portion of the crushed gel particles falling in the particle diameter range of 6 to 20 mesh which accounted for 90 percent of the whole gel was washed with a 0.1M phosphate buffer solution (pH 8.0) to afford 45.6 parts of a gel entrapped microorganism.

At 30° C, 45.6 parts of said gel entrapped microorganism was agitated with 200 parts of an aqueous 1 percent disodium cis-epoxysuccinate solution (pH 7.9) to effect the reaction aimed at. Thereafter, the reaction mixture was filtered to obtain the enzymatic reaction solution. The conversion into disodium L(+)-tartrate as varied with the length of reaction time as observed during the reaction described above is shown in Table 7.

The conversion into disodium L(+)-tartrate to be mentioned hereinbelow is defined by the following formula:

Conversion into disodium L(+)-tartrate =
$$\frac{\text{Number of mols of disodium L(+)-tartrate formed by the enzymatic reaction}}{\text{Number of mols of disodium cis-epoxysuccinate incorporated to the enzymatic reaction system}} \times 100$$

Table 7

| Reaction time (hour) | Conversion into disodium L(+)-tartrate (%) |
| --- | --- |
| 1 | 34 |
| 2 | 64 |
| 3 | 87 |
| 4 | 100 |
| 5 | 100 |

EXAMPLE 45

To 6 parts of the cell suspension obtained similarly to Example 43, 4.5 parts of acrylic acid amide, 0.24 part of N,N'-methylene di(acrylic acid amide), 3 parts of an aqueous 2.5 percent potassium persulfate solution, 3 parts of an aqueous 5 percent β-dimethylaminopropionitrile solution and 24 parts of a 0.1M phosphate buffer solution (pH 8.0) were added and were allowed to polymerize at 30° C for 30 minutes. The polymer gel consequently obtained was pulverized and the portion of the crushed gel particles falling in the particle diameter range of 6 to 20 mesh which accounted for 90 percent of the whole gel was washed with an aqueous 0.1 percent cis-epoxysuccinic acid solution to afford 41.8 parts of a gel entrapped microorganism.

A jacketed column measuring 10 mm in inside diameter and 1000 mm in length was packed with 41.8 parts of the gel entrapped microorganism. At 30° C, an aqueous 5 percent disodium cis-epoxysuccinate solution (pH 8.1) was continuously passed through the column at the flow rate of five parts/hour to obtain an effluent from the column.

When this effluent was analyzed by gas chromatography, a peak corresponding to tartaric acid was observed. On the other hand, 6.5 parts of crystals of dihydrated disodium L(+)-tartrate were obtained by evaporating 100 parts of the column effluent under reduced pressure to dryness (total yield 99 percent). With water, 10 parts of the crystals were dissolved to 50 parts by volume and then tested for specific rotatory power $[\alpha]_D^{20}$, which was shown to be +27.5°. This result is in perfect agreement with that obtained similarly with respect to the super pure grade disodium L(+)-tartrate available on the market. This means that the optical purity of the product was 100 percent.

EXAMPLE 46

A jacketed column measuring 10 mm in inside diameter and 500 mm in length was packed with 21.9 parts of a gel entrapped microorganism obtained similarly to Example 45. At 30° C, an aqueous 2 weight percent disodium cis-epoxysuccinate solution (pH 8.0) was continuously passed through said column at a varying flow rate. The conversion into disodium L(+)-tartrate, conversion rate thereof and concentration thereof in column effluent as varied with the flow rate of the charge are shown in Table 8.

Table 8

| Flow rate (part/hour) | Disodium L(+)-tartrate | | |
| --- | --- | --- | --- |
|  | Conversion (%) | Conversion rate as dihydrate (part/hour) | Concentration as dihydrate in column effluent (%) |
| 2.3 | 92.6 | 0.0278 | 2.42 |
| 4.6 | 59.9 | 0.0360 | 1.57 |
| 11.9 | 21.1 | 0.0328 | 0.55 |
| 21.2 | 15.3 | 0.0424 | 0.40 |
| 31.8 | 11.2 | 0.0465 | 0.29 |

EXAMPLE 47

A jacketed column measuring 10 mm in inside diameter and 500 mm in length was packed with 18 parts of a gel entrapped microorganism obtained similarly to Example 44. A substrate solution (pH 8.0) obtained by dissolving 1.57 parts of disodium cis-epoxysuccinate and 0.01 part of dodecyl trimethyl ammonium chloride in 100 parts of a 0.1M phosphate solution (pH 8.0) was continuously passed through the column at 20° C for 336 hours, with the flow rate fixed at 12.5 parts/hour. Throughout the entire period of the operation, the conversion into disodium L(+)-tartrate was 97.5 percent.

EXAMPLE 48

The procedure of Example 44 was faithfully repeated, except the washing of the crushed polymer gel was made by using an aqueous 0.1 percent disodium cis-epoxysuccinate solution in place of the phosphate buffer solution, to afford 18 parts of a gel entrapped microorganism. A jacketed column measuring 10 mm in inside diameter and 500 mm in length was packed with said gel entrapped microorganism. An aqueous solution containing 1.72 percent of disodium cis-epoxysuccinate and 100 ppm of dodecyl trimethyl ammonium chloride (pH 8.0) was continuously passed through the column at 30° C for 336 hours, with the flow rate fixed at 11 parts/hour. Throughout the entire period of the operation, the conversion into disodium L(+)-tartrate was 100 percent.

When the column effluent was analyzed by gas chromatography, a peak corresponding to tartaric acid was observed. When 100 parts of the column effluent was evaporated to dryness under reduced pressure, there was obtained 2.2 parts of dihydrated disodium L(+)-tartrate in the form of crystals (total yield 99 percent). The crystals were found to have an optical purity of 100 percent.

EXAMPLE 49

When the procedure of Example 43 was repeated by using N-methylol acrylic acid amide, ammonium persulfate and N,N,N',N'-tetramethyl ethylenediamine respectively in place of acrylic acid amide, potassium persulfate and β-dimethylaminopropionitrile, there was similarly obtained a gel entrapped microorganism. The activity yield of the gel entrapped microorganism was found to be 30.9 percent.

EXAMPLE 50

The procedure of Example 43 was repeated, except the polymerization temperature was changed from 30° to 20° C or 40° C, to afford a gel entrapped microorganism. The activity yield of the gel entrapped microorganism thus obtained is shown in Table 9.

Table 9

| Polymerization temperature (° C) | Activity yield (%) |
|---|---|
| 20 | 56.7 |
| 40 | 59.7 |

EXAMPLE 51

By faithfully repeating the procedure of Example 48 except for omission of the use of dodecyl trimethyl ammonium chloride, the operation was continued for a long time in an effort to produce disodium L(+)-tartrate. The conversion into disodium L(+)-tartrate as varied with the operation term and the appearance of the column effluent are shown in Table 10. After 72 hours of operation, the conversion began to decline gradually. After elapse of 144 hours of operation, the column effluent became slightly turbid, indicating propagation of extraneous microorganisms. As there was no prospect of obtaining highly pure disodium L(+)-tartrate any longer, the experiment was discontinued after a total of 192 hours of operation. The dihydrated disodium L(+)-tartrate obtained by the procedure of Example 45 from the column effluent collected after 48 hours of continued operation was found to have an optical purity of 100 percent.

Table 10

| Operation term (hour) | Conversion into disodium L(+)-tartrate (%) | Appearance of column effluent |
|---|---|---|
| 24 | 100 | Clear |
| 48 | 100 | Clear |
| 72 | 96 | Clear |
| 96 | 88 | Clear |
| 120 | 76 | Clear |
| 144 | 61 | Slightly turbid |
| 168 | 44 | Slightly turbid |
| 192 | 25 | Slightly turbid |

EXAMPLE 52

The procedure of Example 43 was repeated except the amount of the 0.1M phosphate buffer solution (pH 8.0) during the polymerization reaction was changed from 6 parts to 4 parts. Seven (7) parts of the gel entrapped microorganism consequently obtained was mixed with 10 parts of an aqueous 2 percent disodium cis-epoxysuccinate solution (pH 8.0) and agitated at a varying temperature for two hours to effect the reaction aimed at, to produce disodium L(+)-tartrate. The relative conversion into disodium L(+)-tartrate as varied with the temperature of enzymatic reaction is shown in Table 11. The relative conversion into disodium L(+)-tartrate shown in Table 11 is defined by the following formula:

Relative conversion =
$$\frac{\text{Conversion into disodium L(+)-tartrate at a given temperature}}{\text{Conversion into disodium L(+)-tartrate at 35° C}} \times 100$$

Table 11

| Reaction temperature (° C) | Relative conversion into disodium L(+)-tartarate |
|---|---|
| 20 | 41 |
| 30 | 76 |
| 35 | 100 |
| 40 | 82 |
| 50 | 36 |

EXAMPLE 53

Seven (7) parts each of a gel entrapped microorganism obtained by following the procedure of Example 47 was added to solutions obtained by dissolving 0.2 part of disodium cis-epoxysuccinate in ten parts of 0.1M phosphate buffer solutions of various pH values and agitated at 30° C for 2 hours to effect the reaction aimed at, to afford disodium L(+)-tartrate. In this case, the 0.1M phosphate buffer solutions of pH 6.0, pH 7.2 and pH 9.0 were those obtained by diluting with water to twice the original volume, the mixed solutions consisting of an aqueous 0.2M monosodium dihydrogen phosphate solution and an aqueous 0.2M disodium monohydrogen phosphate solution at voluminal ratios of 877/123, 28/72 and 6/944 respectively. The relationship between the pH value of the buffer solution used and the relative conversion into disodium L(+)-tartrate as observed in this experiment is shown in Table 12. The relative conversion into L(+)-tartaric acid shown in Table 12 is defined by the following formula.

Relative conversion into disodium L(+)-tartrate =
$$\frac{\text{Conversion into disodium L(+)-tartrate at a given pH value}}{\text{Conversion into disodium L(+)-tartrate at pH 7.2}} \times 100$$

Table 12

| pH value of buffer solution | Relative conversion into disodium L(+)-tartrate |
|---|---|
| 6.0 | 33 |
| 7.2 | 100 |
| 8.0 | 90 |
| 9.0 | 55 |

EXAMPLE 54

A jacketed column measuring 10 mm in inside diameter and 500 mm in length was packed with 18 parts of a gel entrapped microorganism obtained by following the procedure of Example 44. A substrate solution (pH 8.0) obtained by dissolving 1.8 parts of disodium cis-epoxysuccinate and 0.01 part of dodecyl trimethyl ammonium chloride in 100 parts of a 0.05M phosphate buffer solution (pH 8.0) was continuously passed through said column at 30° C for 336 hours, with the flow rate fixed at 10 parts/hour. Throughout the entire period of the operation, the conversion into disodium L(+)-tartrate was 100 percent.

EXAMPLE 55

Three (3) jacketed columns measuring 10 mm in inside diameter and 1000 mm in length was packed each with 36 parts of a gel entrapped microorganism obtained by following the similar procedure to Example 44. Solution "A" (pH 8.0) (obtained by dissolving 10 parts of disodium cis-epoxysuccinate and 0.01 part of dodecyl trimethyl ammonium chloride in 100 parts of water), solution "B" (pH 8.0) (obtained by dissolving 10 parts of disodium cis-epoxysuccinate and 0.01 part of dodecyl trimethyl ammonium chloride in 100 parts of 0.025M phosphate buffer solution of pH 8.0) and solution "C" (pH 8.0) (obtained by dissolving 10 parts of disodium cis-epoxysuccinate and 0.01 part of dodecyl trimethyl ammonium chloride in 100 parts of 0.025M tris buffer solution of pH 8.0) were continuously passed as the substrate solution through said columns, respectively, at 30° C, with the flow rate fixed at 6 parts/hour.

Each one kg of the column effluent was taken and, while it was kept under agitation at normal room temperature, an aqueous 20 percent calcium chloride solution was dropwise introduced therein until occurrence of new precipitate stopped. For two hours, the agitation was further continued. The mixture thus obtained was centrifuged for 20 minutes to separate the precipitate. The precipitate thus obtained was dispersed in 150 ml of water. The dispersion was centrifuged for 20 minutes, with the resultant supernatant discarded. This washing treatment was repeated twice. The clean precipitate was dispersed in 50 ml of water and, while it was kept under agitation at 20° C, concentrated sulfuric acid was introduced dropwise therein until the pH value became 1.8. The resultant mixture was centrifuged for 20 minutes to produce a supernatant, which was dried up. Consequently, crystals of L(+)-tartaric acid were obtained. The results are shown in Table 13.

Table 13

| Substrate solution | L(+)-tartaric acid | | | |
|---|---|---|---|---|
| | Yield (%) | Purity (%) | Impurities (%) | |
| | | | Phosphate ion | Nitrogen content |
| Solution "A" | 94.0 | 99.7 | less than 0.00001 | Less than 0.00001 |
| Solution "B" | 93.5 | 98.9 | 0.68 | Less than 0.00001 |
| Solution "C" | 93.7 | 99.6 | Less than 0.00001 | 0.0003 |

What we claim is:

1. A process for the manufacture of L(+)-tartaric acid or salts thereof, which comprises contacting cis-epoxysuccinic acid or a salt thereof with a substance containing cells of a microorganism belonging to the genus Acetobacter or the genus Corynebacterium having cis-epoxysuccinic acid-hydrolyzing activity, or a treated product thereof, in an aqueous medium, and subsequently collecting the produced L(+)-tartaric acid or salts thereof.

2. The process according to claim 1, wherein the microorganism belonging to the genus Acetobacter possesses the ability to effect hydrolysis and ring cleavage of the epoxy group of cis-epoxysuccinic acid or salts thereof and is selected from the group consisting of *Acetobacter curtus* No. 4, *Acetobacter curtus* No. 10 and *Acetobacter curtus* No. 21.

3. The process according to claim 1, wherein the microorganism belonging to the genus Corynebacterium possesses the ability to effect hydrolysis and ring cleavage of the epoxy group of cis-epoxysuccinic acid or salts thereof and is Corynebacterium S-13.

4. The process according to claim 1, wherein the salt of cis-epoxysuccinic acid is selected from the group consisting of the sodium salts, potassium salts, sodium-potassium salts, calcium salts, sodium-calcium salts, magnesium salts, iron salts, aluminum salts, zinc salts, manganese salts, ammonium salts, sodium-ammonium salts, methylamine salts and triethylamine salts thereof.

5. The process according to claim 1, wherein said contacting is conducted at a pH of from 4 to 10.

6. The process according to claim 1, wherein said contacting is conducted at a temperature of not more than 65° C.

7. The process according to claim 1, wherein the substance containing the microorganism cells is a gel obtained by allowing an acrylic acid amide type monomer to undergo polymerization in a reaction mixture containing said microorganism.

8. The process according to claim 7, wherein the polymerization is conducted in the presence of a polymerization accelerator.

9. The process according to claim 7, wherein the polymerization is conducted in the presence of a polymerization is conducted in the presence of a polymerization initiator.

10. The process according to claim 1, wherein the microorganism belongs to the genus Acetobacter.

11. The process according to claim 10, wherein said Acetobacter microorganism is catalase-negative.

12. The process according to claim 1, wherein the microorganism belongs to the genus Corynebacterium.

* * * * *